(12) United States Patent
Mitamura et al.

(10) Patent No.: US 8,801,603 B2
(45) Date of Patent: Aug. 12, 2014

(54) ENDOSCOPE

(71) Applicant: Olympus Medical Systems Corp., Tokyo (JP)

(72) Inventors: Yuki Mitamura, Hachioji (JP); Takeshi Ogura, Hamburg (DE); Toshihiro Hadano, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/765,053

(22) Filed: Feb. 12, 2013

(65) Prior Publication Data

US 2013/0150667 A1    Jun. 13, 2013

Related U.S. Application Data

(63) Continuation of application No. PCT/JP2012/061636, filed on May 7, 2012.

(30) Foreign Application Priority Data

Sep. 5, 2011   (JP) .................. 2011-192866

(51) Int. Cl.
*A61B 1/04* (2006.01)
*A61B 1/00* (2006.01)

(52) U.S. Cl.
CPC ............... *A61B 1/00064* (2013.01); *A61B 1/0008* (2013.01)
USPC ........................................ 600/130; 600/134

(58) Field of Classification Search
CPC ... A61B 1/00; A61B 1/00071; G02B 23/2476
USPC ............. 600/129, 134, 104, 130; 348/45; 356/241.5; 362/574; 385/117
See application file for complete search history.

(56) References Cited

U.S. PATENT DOCUMENTS

2008/0051634 A1* 2/2008 Yamashita et al. ............ 600/134
2009/0048490 A1* 2/2009 Iijima ........................... 600/180

FOREIGN PATENT DOCUMENTS

| JP | 03-063025 | 3/1991 |
| JP | 03-280918 | 12/1991 |
| JP | 09-173280 | 7/1997 |
| JP | 2006-122498 | 5/2006 |

OTHER PUBLICATIONS

Extended Supplementary European Search Report dated Feb. 27, 2014 from related European Application No. 12 83 0404.5.

* cited by examiner

*Primary Examiner* — Alireza Nia
*Assistant Examiner* — Timothy J Neal
(74) *Attorney, Agent, or Firm* — Scully, Scott, Murphy & Presser, P.C.

(57) ABSTRACT

An endoscope of an embodiment includes: a distal end rigid member made of resin; a channel tube connecting member which has a distal end side fitted and fixed in the distal end rigid member and is formed in a tubular shape using a conductive member, and which includes a stepped portion on a part of an outer circumferential surface in a longitudinal direction; and a bending piece member which is formed in a tubular shape using a conductive member and arranged just behind a rear end side of the distal end rigid member, and which has a protruding portion protruding and elastically-deformed toward an inner circumferential surface side, wherein when the bending piece member is fixed to the distal end rigid member with the channel tube connecting member being housed inside thereof, the protruding portion contacts the outer circumferential surface of the channel tube connecting member to establish conduction.

8 Claims, 8 Drawing Sheets

ENDOSCOPE

This application is a continuation application of PCT/JP2012/061636 filed on May 7, 2012 and claims benefit of Japanese Application No. 2011-192866 filed in Japan on Sep. 5, 2011, the entire contents of which are incorporated herein by this reference.

BACKGROUND OF THE INVENTION

1. Field of the Invention

The present invention relates to an endoscope including an insertion channel in an insertion portion.

2. Description of the Related Art

Conventionally, endoscopes have been widely used in a medical field, and the like. There is a desire for an endoscope having a distal end portion of a reduced diameter in order to alleviate pain of a patient at the time of examination. It is indispensable for a transnasal endoscope, in particular, which performs treatment and therapy by nasally inserting an insertion portion from the nose, to reduce the diameter size of a distal end portion.

Treatment and therapy are performed by inserting a treatment instrument such as a forceps into an insertion channel provided in the insertion portion of such an endoscope.

However, according to an endoscope in which a distal end rigid member as a main constituting member of a distal end portion is made of metal, when treatment and therapy are performed by inserting a high-frequency treatment instrument into an insertion channel, it would be likely that a leakage current caused by high-frequency output of the high-frequency treatment instrument flows in a body of a patient through a distal end rigid member.

Therefore, an endoscope including an insulating distal end cover configured to cover a metallic distal end rigid member is proposed in prior arts.

In addition, when an image pickup device is fixed to a metallic distal end portion (irrespective of presence or absence of the distal end cover), there is a possibility that a leakage current at the time of high-frequency treatment will flow in the image pickup device through a metallic portion of a distal end member. As a result, noise is likely to occur in an output signal of the image pickup device.

Therefore, an endoscope is proposed in which a size reduction of a distal end outer diameter is realized by configuring a distal end rigid member by resin and a leakage current caused by high-frequency output is prevented from easily flowing in an image pickup device.

For example, Japanese Patent Application Laid-Open Publication No. 2006-122498 discloses a configuration related to an endoscope which includes a distal end rigid member made of resin, a metallic connecting pipe fixed to the distal end rigid member, and a distal-most joint ring (also referred to as a bending piece) which is soldered to a rear end portion of the connecting pipe to be electrically connected to the connecting pipe, wherein a leakage current caused by high-frequency output of the high-frequency treatment instrument is allowed to flow to a ground member of an insertion portion, such as a joint ring of a bending portion, through the connecting pipe.

Furthermore, a conventional endoscope including a distal end rigid member made of metal and a distal end cover configured to cover the distal end rigid member has usually achieved a conduction between the distal end rigid member and a joint ring and prevented the joint ring from falling off to a forward side of the distal end rigid member by fixing the distal-most side joint ring to the distal end rigid member by mounting using a screw and the like.

SUMMARY OF THE INVENTION

An endoscope according to one aspect of the present invention includes: a distal end rigid member made of resin and including a communicating hole for an insertion channel; a channel tube connecting member formed in a tubular shape using a member having conductivity, the channel tube connecting member having a distal end side fitted and fixed in the communicating hole of the distal end rigid member and a rear end side connected to an insertion channel tube; a bending piece member formed in a tubular shape using a member having conductivity, the bending piece member being fixed to just behind a rear end side of the distal end rigid member with the channel tube connecting member being housed inside the bending piece member; and a protruding portion provided on a circumferential surface of one of the channel tube connecting member and the bending piece member and configured to elastically protrude toward a circumferential surface of the other of the channel tube connecting member and the bending piece member, the protruding portion contacting the circumferential surface of the other of the channel tube connecting member and the bending piece member to establish conduction when the bending piece member is fixed to the distal end rigid member with the channel tube connecting member being housed inside of the bending piece member.

DETAILED DESCRIPTION OF THE PREFERRED EMBODIMENT(S)

Hereinafter, embodiments of the present invention will be described in detail with reference to drawings.

(First Embodiment)

Figure 1:
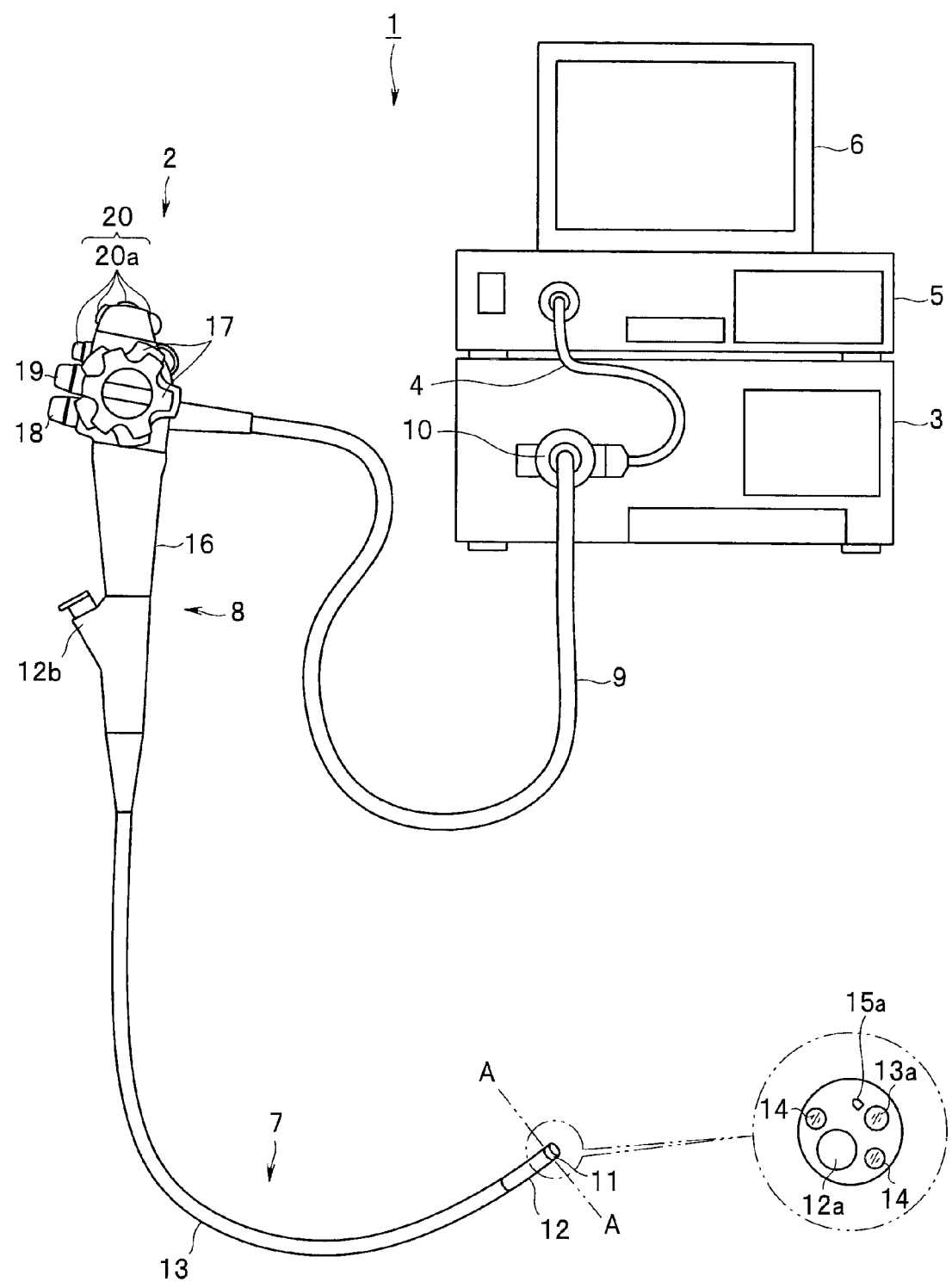
FIG. 1 is a block diagram illustrating an overall configuration of an endoscope system according to a first embodiment of the present invention.

FIG. 1 is a block diagram illustrating an overall configuration of an endoscope system according to a first embodiment of the present invention.

As shown in FIG. 1, an endoscope system 1 of the present embodiment is configured by including an endoscope 2, a light source device 3, a video processor 5, and a color monitor 6.

The endoscope 2 includes an insertion portion 7 and an operation portion 8 from which the insertion portion 7 is extended, and a universal cord 9 which is extended from the operation portion 8 and connected to the light source device 3 through a scope connector 10. In addition, the scope connector 10 is detachably connected with an electric connector of one end portion of a scope cable 4. Furthermore, an electric connector of the other end of the scope cable 4 is connected to a video processor 5.

The insertion portion 7 includes consecutively in the following order from the distal end: a distal end portion 11 as a distal end rigid portion; a bending portion 12; and a flexible tube portion 13. On a distal end surface of the distal end portion 11, a distal end opening portion 12a, an observation window 13a, two illumination windows 14, and an observation window cleaning nozzle 15a are disposed.

On a rear surface side of the observation window 13a, an image pickup apparatus 50 (See FIG. 2) incorporated in the distal end portion 11 is disposed. In addition, on rear surface sides of the two illumination windows 14, light guide bundles 32 (See FIG. 3) which transmit illumination light from the light source device 3 and which are inserted in the universal cord 9 from the distal end portion 11 are disposed.

An air/water feeding tube 15A, which is inserted in the universal cord 9 from the distal end portion 11, is connected and fixed to the observation window cleaning nozzle 15a, through a connecting pipe, not shown. The air/water feeding tube 15A is connected to an air/water feeding tank in which cleaning water is stored and a compressor, which are not shown, on the side of the light source device 3.

The operation portion 8 includes a forceps port 12b and a grip portion 16 disposed at a side portion on a lower side of the operation portion, and includes, at an upper side thereof, two bending operation portions 17, an air/water feeding control portion 18, a suction control portion 19, and a switch portion 20 which is configured by a plurality of switches 20a and which mainly operates an image pickup function. Note that the forceps port 12b of the operation portion 8 and the distal end opening portion 12a of the insertion portion 7 configure an opening portion of an insertion channel disposed in the insertion portion 7.

Next, a configuration of the distal end portion 11 of the endoscope 2 according to the present embodiment will be described with reference to FIGS. 2 to 5.

As shown in FIGS. 2 to 5, the distal end portion 11 of the endoscope 2 according to the present embodiment is configured by including a distal end rigid member 21 as a main constituting member of the distal end portion 11, a channel tube connecting member 22, and a bending piece member 23.

Figure 4:
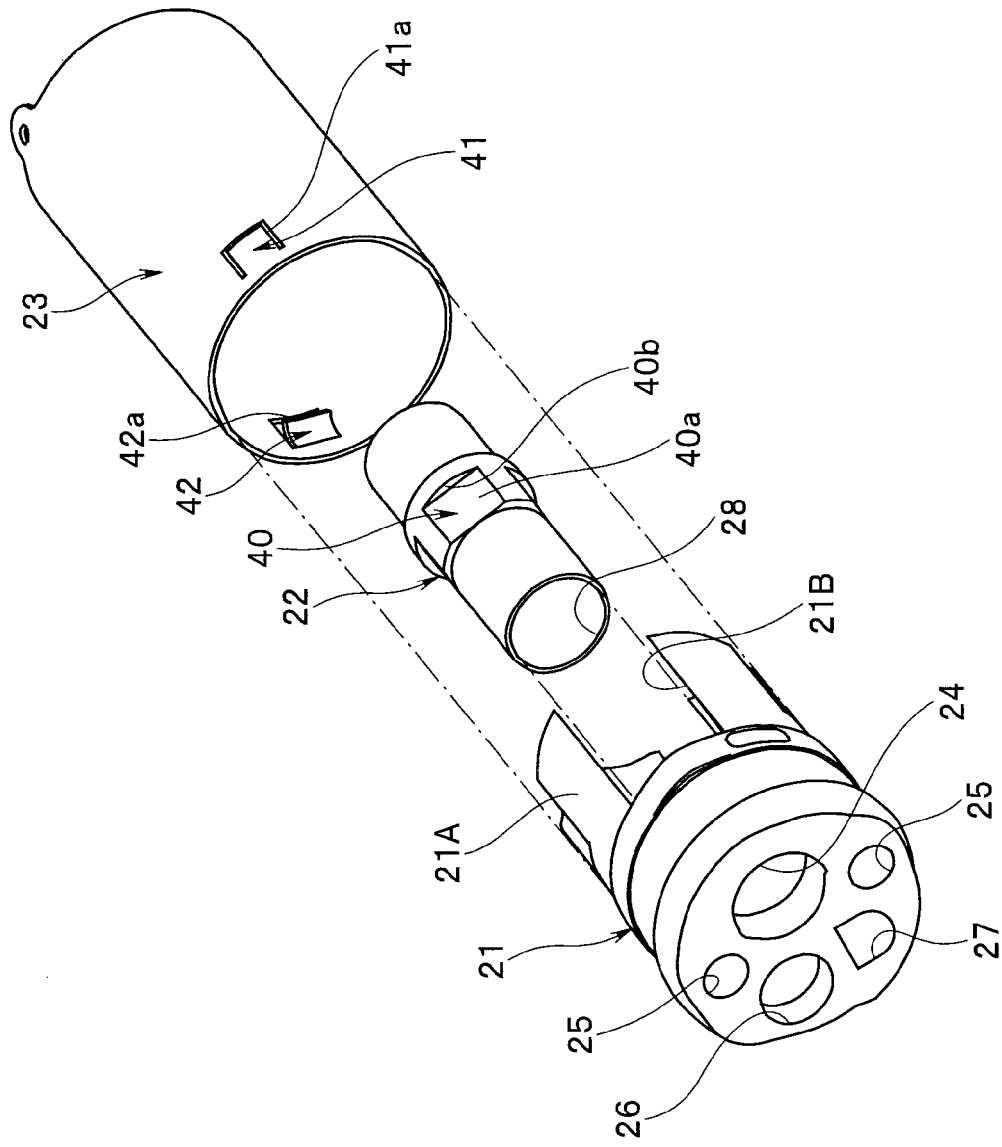
FIG. 4 is an exploded perspective view illustrating a state where a distal end rigid member, a channel tube connecting member, and a distal-most bending piece member in FIG. 3 are disassembled.

The distal end rigid member 21 configures a distal end portion main body made of resin, and includes one opening portion 24 and three communicating holes 25 to 27, as shown in FIG. 4.

The opening portion 24 is an opening portion of a communicating hole for an insertion channel 28. The two communicating holes 25 are communicating holes for allowing the glass lenses 31 configuring the illumination windows 14 and the light guide bundles 32 to be inserted therein from the distal ends and disposed therein. The communicating hole 26 is a communicating hole in which an optical system of the image pickup apparatus 50 and the observation window 13a disposed in front of the optical system are inserted and attached. In addition, the communicating hole 27 is a communicating hole to which the observation window cleaning nozzle 15a is attached, and on a rear end side of the communicating hole 27, a connecting pipe, not shown, which is connected to the air/water feeding tube 15A is fitted.

Figure 3:
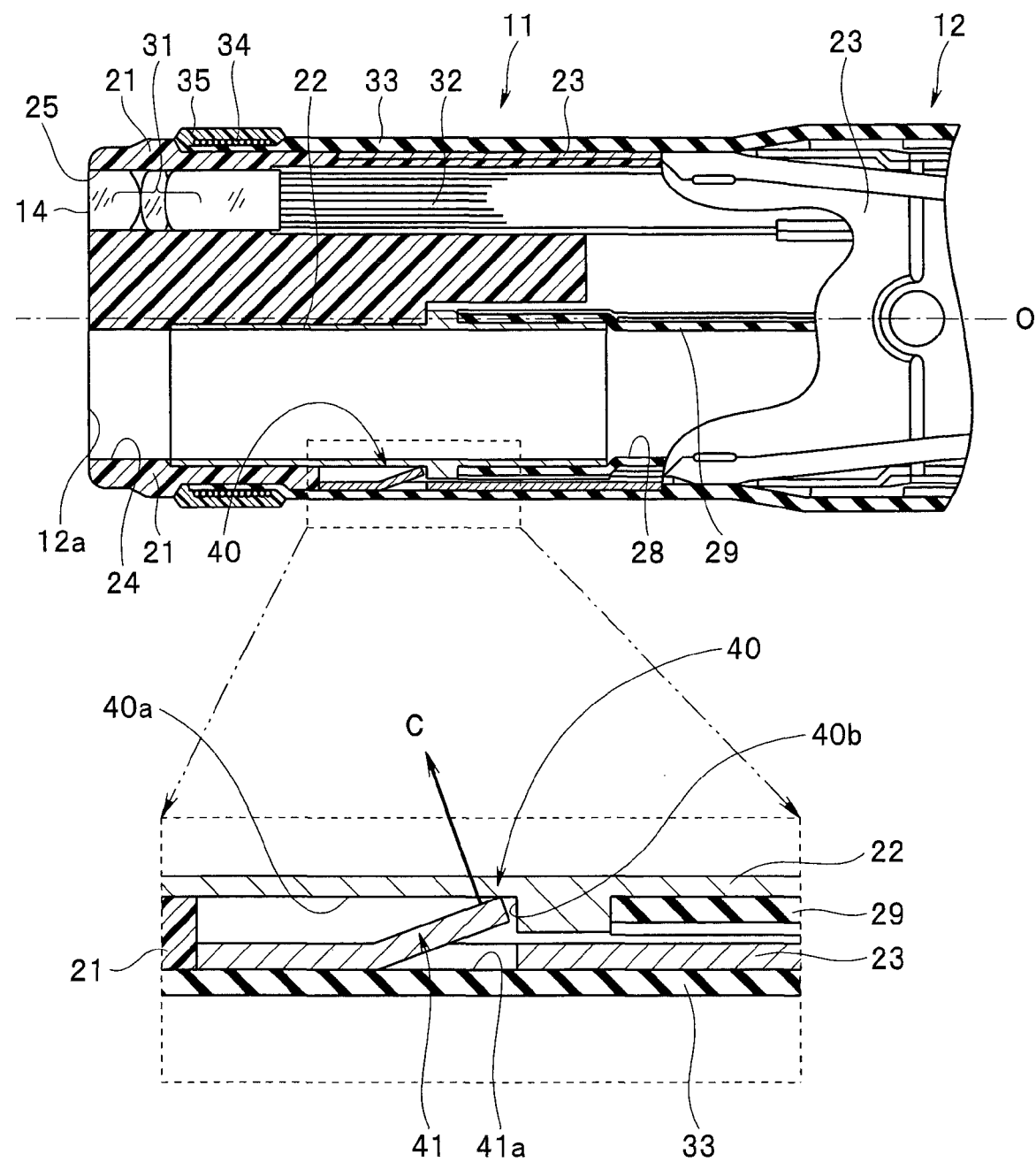
FIG. 3 illustrates a configuration of a main part of the endoscope according to the first embodiment, and is a cross-sectional view taken along B-B line in FIG. 2.

As shown in FIG. 3, a distal end side of the channel tube connecting member 22 is inserted in a rear end side of the opening portion 24 of the distal end rigid member 21 and adhered and fixed thereto using adhesive and the like. An insertion channel tube 29 is connected to a rear end side of the channel tube connecting member 22. The channel tube connecting member 22 is formed in a tubular shape using a member having conductivity.

The transparent glass lenses 31 which configure the illumination windows 14 are fixed respectively to the two communicating holes 25 of the distal end rigid member 21. Furthermore, at the rearward of the glass lenses 33, the distal end parts of the light guide bundles 32 arranged in the insertion portion 7 are respectively disposed. The illumination light transmitted from the light source device 3 by the light guide bundles 32 is thus emitted to a forward side of the distal end portion 11 through the glass lenses 31 (illumination windows 14).

In addition, the optical system (not shown) of the image pickup apparatus 50 and the observation window 13a arranged in front of the optical system are fixed to the communicating hole 26 of the distal end rigid member 21. Furthermore, the connecting pipe, not shown, to which the air/water feeding tube 15A (see FIG. 2) is connected is fitted in the communicating hole 27 of the distal end rigid member 21, and on the distal end side of the communicating hole 27, the observation window cleaning nozzle 15a is attached.

As shown in FIGS. 3 and 4, the bending piece member 23 is a bending piece member which is formed in a tubular shape using a member having conductivity and arranged just behind the rear end side of the distal end rigid member 21, and the bending piece member 23 is fixed onto the proximal end side of the distal end rigid member 21 with the channel tube connecting member 22 being housed inside thereof. Note that the bending portion 12 is made of a plurality of bending piece members including the bending piece member 23, and configured to bend in up, down, left and right directions by four operation wires, not shown, and the bending operation portion 17 of the operation portion 8.

Figure 2:
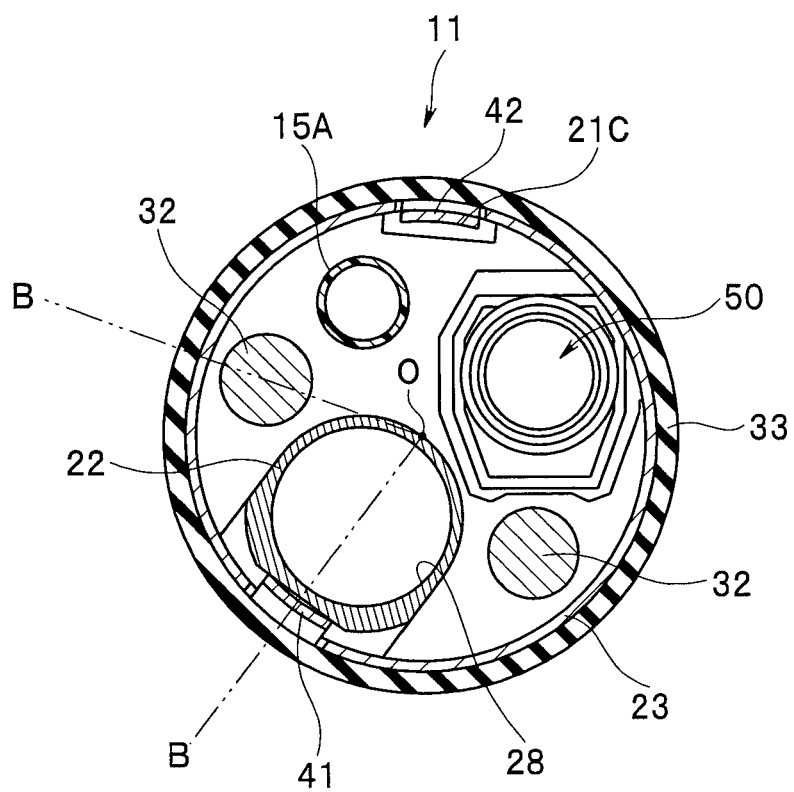
FIG. 2 is a cross-sectional view of a distal end rigid member of an endoscope taken along A-A line in FIG. 1.

In addition, as shown in FIGS. 2 and 3, a distal end insertion rubber member 33 which integrally covers an outer circumference of the distal end rigid member 21 and a plurality of bending piece members 23 in the bending portion 12 so as to form the outer shape of the distal end portion 11 and the bending portion 12. A distal end outer circumferential portion of the distal end insertion rubber member 33 is fixed to the distal end rigid member 21 by a spool portion 34. Furthermore, an adhesive 35 is applied so as to cover an outer circumference of the spool portion 34.

In the endoscope 2 according to the present embodiment, the channel tube connecting member 22 is configured by including a stepped portion 40 on a part of the outer circumferential surface in the longitudinal direction, the bending piece member 23 includes a protruding portion 41 which protrudes toward the inner circumferential surface side and elastically deforms toward the inner circumferential surface side, and the protruding portion 41 is configured to contact the stepped portion 40 when the bending piece member 23 houses the channel tube connecting member 22 inside thereof and fixed to the distal end rigid member 12, thereby establishing conduction.

Figure 5:
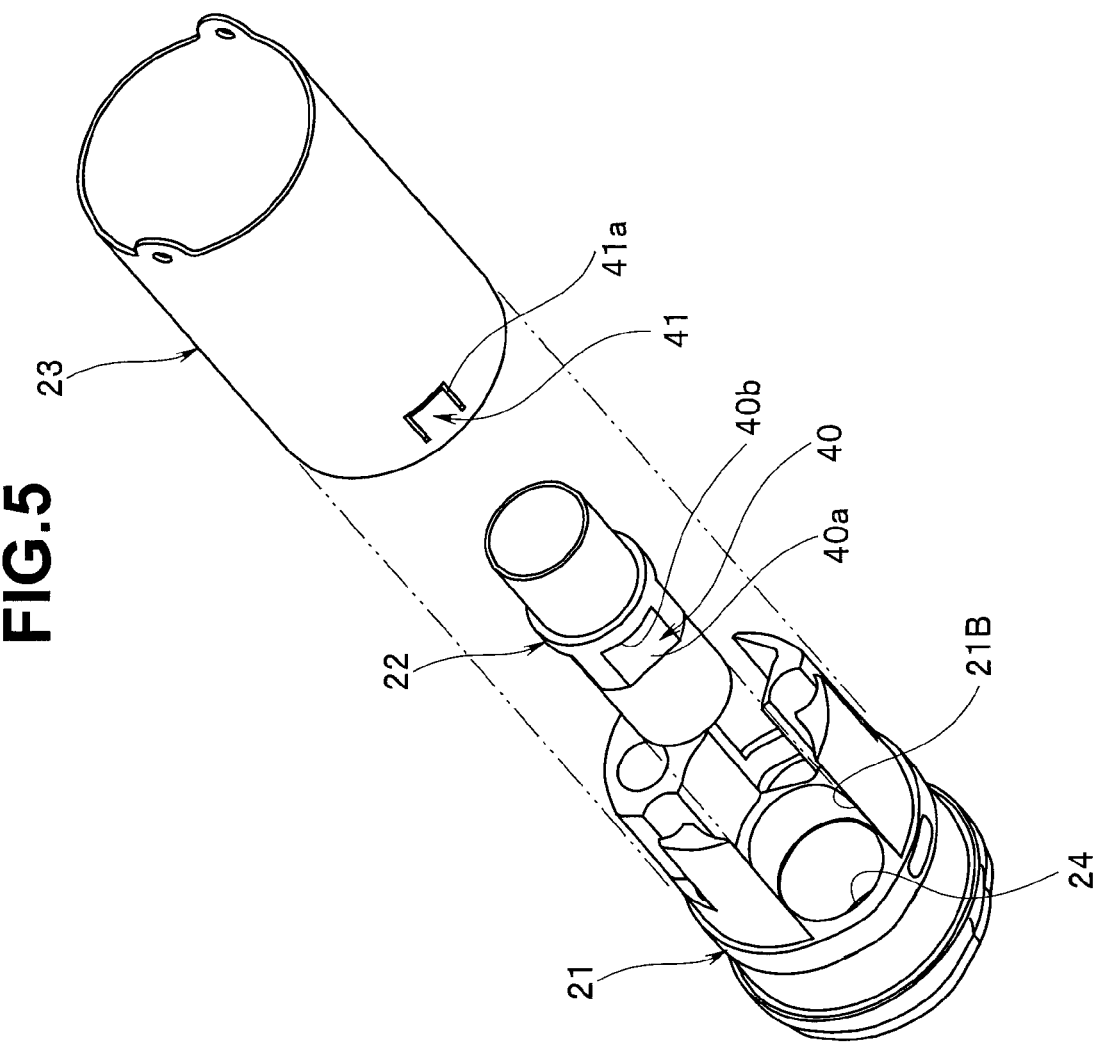
FIG. 5 is an exploded perspective view when viewed from rearward of the bending piece member in FIG. 4.

To describe more in detail, as shown in FIGS. 3 to 5, the stepped portion 40 of the channel tube connecting member 22 is configured by including a contacting surface 40a which is parallel with respect to a central axis O and a wall portion 40b formed along a direction perpendicular to the contacting surface 40a.

On the other hand, the protruding portion 41 of the bending piece member 23, which contacts the stepped portion 40, is formed by providing a cutout 41a having a squared U-shape at a thin-walled portion of the bending piece member 23, for example, and the protruding portion is plastic-deformed by being pushed out toward the inner circumferential surface side. The plastic-deformed protruding portion 41 has an elastic force, though the protruding portion 41 is configured integrally with the bending piece member 23.

In addition, another protruding portion 42 for fall-off prevention is provided on a circumferential surface opposed to the protruding portion 41. The protruding portion 42 is configured similarly as the protruding portion 41. Note that the protruding portion 42 is configured to be latched into a latching groove portion 21C (see FIG. 2) provided on the outer circumferential surface of the distal end rigid member 21, when the bending piece member 23 is fixed to the distal end rigid member 21 with the channel tube connecting member 22 being housed inside the bending piece member 23.

Next, an assembling procedure and working of the main part of the distal end portion 11 configured as described above are described with reference to FIGS. 3 to 7.

A worker previously attaches the above-described glass lenses 31, the light guide bundles 32, the air/water feeding tube 15A, and the image pickup apparatus 50 respectively to the one opening portion 24 and the four communicating holes 25 to 27 of the distal end rigid member 21.

Then, the worker inserts the distal end side of the channel tube connecting member 22 into the opening portion 24 of the distal end rigid member 21 to bond and fix the distal end side of the channel tube connecting member 22 to the opening portion 24 using adhesive or the like.

At this time, the stepped portion 40 of the channel tube connecting member 22 is arranged so as to be exposed from a cutout 21B provided at a rear end portion 21A of the distal end rigid member 21. Then, the insertion channel tube 29 provided so as to extend from the insertion portion 7 is connected to the rear end side of the channel tube connecting member 22 with adhesive or the like.

After that, the worker fits and mounts the bending piece member 23 located on the side of the insertion portion 7 into the rear end portion 21A of the distal end rigid member 21 with the channel tube connecting member 22 being housed inside the bending piece member 23.

In this case, the worker performs the mounting while performing positioning such that the protruding portion 41 of the bending piece member 23 fits along a cutout 21B of the distal end rigid member 21. It is only necessary to mount the bending piece member 23 to the rear end portion 21A of the distal end rigid member 21 using adhesive or the like.

When the bending piece member 23 is completely fitted into the rear end portion 21A of the distal end rigid member 21 to be fixed thereto, in the present embodiment, as shown in FIG. 3, the protruding portion 41 of the bending piece member 23 contacts the contacting surface 40a of the channel tube connecting member 22 due to an elastic force of the protruding portion.

At this time, the protruding portion 41 is constantly biased by the elastic force of itself in the direction of arrow C shown in FIG. 3, so that the contact between the protruding portion 41 and the contacting surface 40a of the channel tube connecting member 22 can be surely maintained. That is, the conduction state between the channel tube connecting member 22 and the bending piece member 23 can be ensured. Note that the protruding portion 41 is configured to contact the stepped portion 40 within a range of the cutout 21B of the distal end rigid member 21 in the longitudinal direction.

In addition, the other protruding portion 42 of the bending piece member 23 is latched into the latching groove portion 21C (see FIG. 2) of the distal end rigid member 21. Also in this case, the protruding portion 42 is biased so as to constantly latch into the latching groove portion 21C by an elastic force of the protruding portion 42, thereby capable of maintaining the latched state.

Then, the worker fixes the bending piece member 23 to the distal end rigid member 21, and thereafter, as shown in FIG. 2, provides the distal end insertion rubber member 33 so as to integrally cover the outer circumference of the distal end rigid member 21 and the plurality of bending piece members 23 in the bending portion 12, fixes the distal end outer circumferential portion of the distal end insertion rubber member 33 to the distal end rigid member 21 by the spool portion 34, and furthermore applies the adhesive 35 so as to cover the outer circumference of the spool portion 34, to thereby configure the distal end portion 11 and the bending portion 12.

Now, it is supposed that a high-frequency treatment instrument, not shown, is inserted into the insertion channel 28 of the endoscope 2 according to the present embodiment, and treatment is performed. At this time, if the treatment is performed in a conductive liquid such as normal saline using a high-frequency treatment instrument, a leakage current of the high-frequency output is likely to be generated.

However, the endoscope 2 according to the present embodiment can manage even the case where the leakage current of the high-frequency power is thus generated. That is, as described above, the stepped portion 40 (contacting surface 40a) of the channel tube connecting member 22 made of a conductive member contacts the protruding portion 41 of the bending piece member 23 made of a conductive member, which establishes electrical conduction therebetween.

Figure 7:
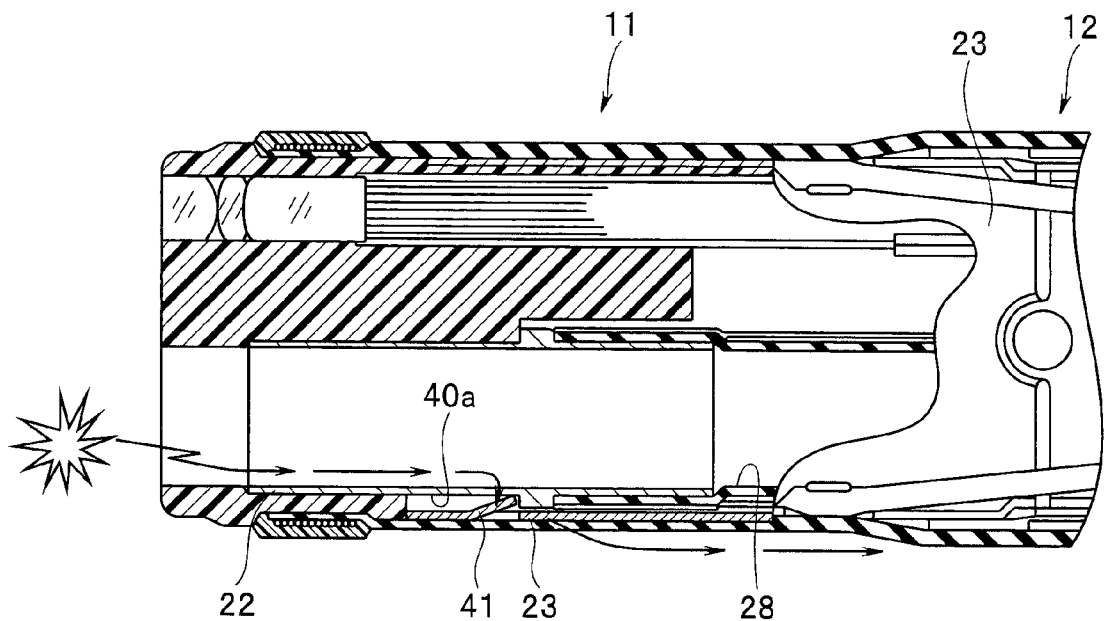
FIG. 7 is an illustration diagram for describing a working of the endoscope according to the first embodiment.

Therefore, as shown in FIG. 7, the leakage current of the high-frequency output flows in the following order as shown by the arrows in FIG. 7: the channel tube connecting member 22→the contacting surface 40a of the stepped portion 40→the protruding portion 41→the bending piece member 23→a bending piece member in a subsequent stage, not shown. Accordingly, the leakage current of the high frequency output can be escaped to a ground member of the insertion portion 7, such as the bending piece member 23.

Figure 6:
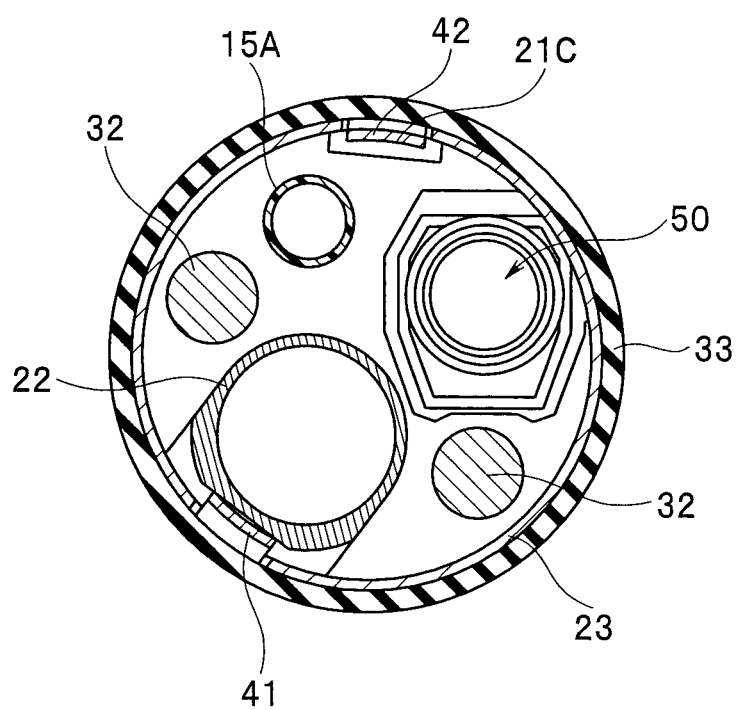
FIG. 6 is a cross-sectional view illustrating a layout of a protruding portion and an image pickup apparatus in a distal end portion.

In addition, as shown in FIGS. 2 and 6, the endoscope 2 of the present embodiment has a configuration in which the protruding portion 41 and the stepped portion 40 are arranged at positions separated away from the image pickup apparatus 50 on the cross section in the direction perpendicular to the axis O of the distal end rigid member 21. Therefore, even if a leakage current of the high frequency power is generated, the leakage current of the high frequency power is not likely to flow into the image pickup device in the image pickup apparatus 50, and as a result, it is possible to prevent noise from generating in the output signal from the image pickup device.

In addition, the endoscope 2 according to the present embodiment is provided with the stepped portion 40 and the protruding portion 41, thereby not only ensuring the conduction state but also providing a function for fall-off prevention.

For example, it is assumed that adhesive is peeled off due to aging degradation and the like at the distal end portion 11 of the endoscope 2, and as a result, the bending piece member 23 comes off from the distal end rigid member 21.

However, in the endoscope 2 according to the present embodiment, the protruding portion 41 of the bending piece member 23 slides on the contacting surface 40a and abuts the wall portion 40b of the channel tube connecting member 22, to be latched thereto. At the same time, the other protruding portion 42 of the bending piece member 23 is latched into the latching groove portion 21C (see FIG. 2) of the distal end rigid member 21.

That is, the protruding portion 41 is latched to the wall portion 40b, and at the same time, the other protruding portion 42 is also latched into the latching groove portion 21C, thereby preventing movement of the bending piece member 23 in the pull-out direction from the distal end rigid member 21 (direction away from the distal end rigid member 21, that is, the rear end side direction (right direction in FIG. 3) of the distal end rigid member 21). That is, it is possible to provide a fall-off prevention function for preventing the bending piece member 23 from coming off from the distal end portion 11, and maintain the conduction state.

Note that, in the present embodiment, the cutout 21B of the distal end rigid member 21, the stepped portion 40 of the channel tube connecting member 22, and the protruding portion 41 of the bending piece member 23 have a function for positioning various kinds of components when assembling the distal end portion 11.

As described above, the endoscope 2 according to the present embodiment is configured such that the protruding portion 41 having the above-described conduction function and the fall-off prevention function is plastic-deformed by only pushing out a part of the circumferential surface of the bending piece member 23 toward the inner circumferential surface side and is allowed to have an elastic force. Accordingly, the protruding portion does not affect the internal components in the distal end portion 11.

Figure 10:
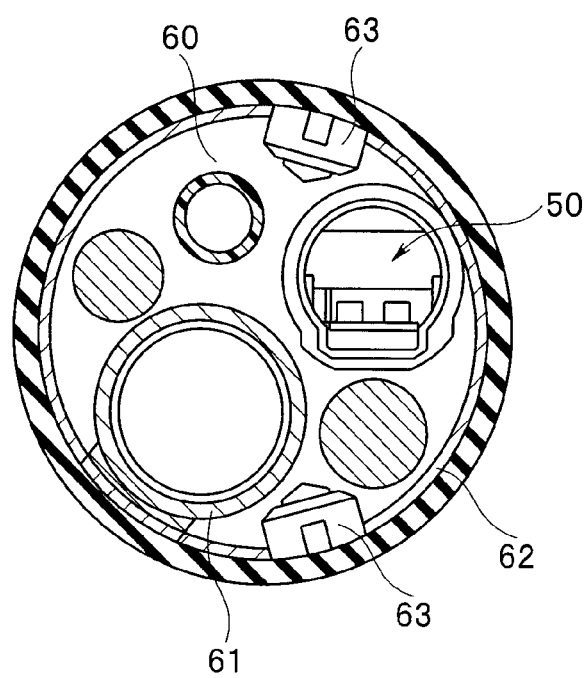
FIG. 10 is a cross-sectional view of a distal end portion of a conventional endoscope.

In addition, in the prior art example shown in FIG. 10, the bending piece member 62 is fixed to the distal end rigid member 60 by using a screw 63. However, in the present embodiment, since the bending piece member 23 can be fixed to the distal end rigid member 21 without using the screw 63, it is possible to achieve the conduction function and the fall-off prevention function in a reduced space.

Such a configuration makes it possible to achieve not only the reduced diameter of the distal end rigid member 21 but also the reduced diameter of the distal end portion 11.

Therefore, according to the first embodiment, it is possible to achieve the endoscope 2 in which the diameter of the distal end rigid member 21 can be reduced and the conduction with respect to the bending piece member 23 of the bending portion 12 can be surely established.

In addition, when the distal end portion 11 of the endoscope 2 is repaired, in the endoscope 2 according to the present embodiment, it is possible to separate the distal end rigid member 23 and the bending piece member 21 from each other by only detaching the protruding portion 41 from the stepped portion 40 and peeling off the adhesive. That is, in contrast to the connecting and fixing by soldering which has been required in prior arts, it is possible to easily detach the bending piece member 23 from the distal end rigid member 21 without a need for work of cleaning off the soldering thoroughly, which improves workability of repair.

Furthermore, the conduction between the channel tube connecting member 22 and the bending piece member 23 can be ensured without using a fixing member such as a screw.

Therefore, it is needless to say that not only the number of components can be reduced, but also the manufacturing process can be simplified because a complicated work such as soldering is not required during assembling. As a result, it is possible to reduce the manufacturing cost.

(Second Embodiment)

Figure 8:
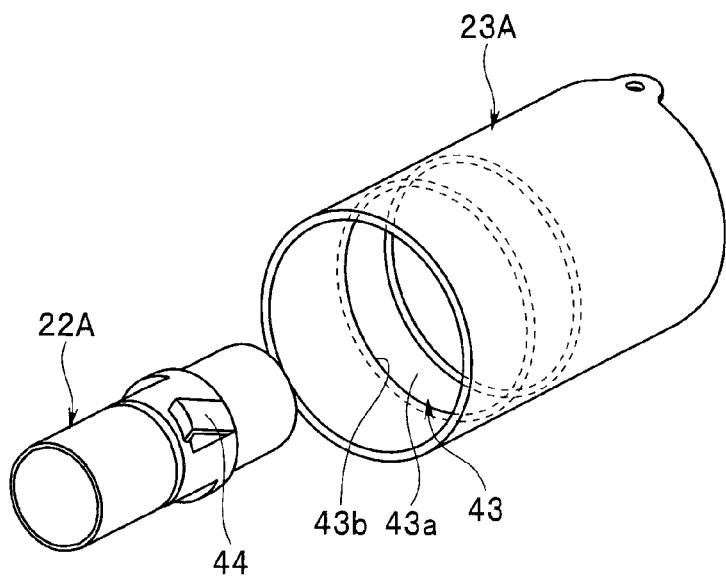
FIG. 8 is an exploded perspective view illustrating a state where a channel tube connecting member and a distal-most bending piece member of an endoscope according to a second embodiment of the present invention are disassembled.
Figure 9:
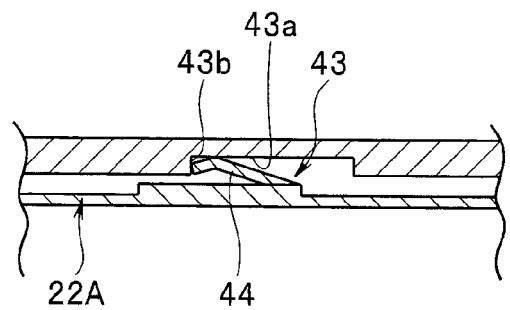
FIG. 9 is an enlarged view illustrating a configuration of the protruding portion and a stepped portion in FIG. 8.

FIG. 8 is an exploded perspective view illustrating a state where a channel tube connecting member and a distal-most bending piece member of an endoscope according to a second embodiment of the present invention are disassembled, and FIG. 9 is an enlarged view illustrating a configuration of the protruding portion and a stepped portion in FIG. 8. Note that, in FIGS. 8 and 9, the same constituent elements as those in the endoscope 2 according to the first embodiment are attached with the same reference numerals and descriptions thereof will be omitted, and only different parts are described.

The endoscope 2 according to the present embodiment is configured such that the protruding portion according to the first embodiment is provided to the channel tube connecting member 22 and the stepped portion is provided to the bending piece member 23.

Specifically, as shown in FIG. 8, the endoscope 2 according to the present embodiment includes a channel tube connecting member 22A including a protruding portion 44 and a bending piece member 23A including a stepped portion 43.

Similarly in the first embodiment, the channel tube connecting member 22A is formed in a tubular shape using a member having conductivity, and has a distal end side fitted and fixed in the communicating hole 25 of the distal end rigid member 21, and a rear end side connected to an insertion channel tube 29.

The protruding portion 44 of the channel tube connecting member 22A is configured to protrude toward the outer circumferential surface side and elastically deform toward the outer circumferential surface side.

On the other hand, similarly as in the first embodiment, the bending piece member 23A is a bending piece member which is fixed to the distal end rigid member 21 with the channel tube connecting member 22A housed inside thereof and which is formed in a tubular shape using a member having conductivity and arranged just behind the rear end side of the distal end rigid member 21.

The stepped portion 43 of the bending piece member 23A is provided on a part of the inner circumferential surface in the longitudinal direction. The bending piece member 23A is configured such that the protruding portion 44 and the stepped portion 43 are brought into contact with each other to establish a conduction when the bending piece member 23A is fixed to the distal end rigid member 21 with the channel tube connecting member 22A housed inside thereof.

To describe more in detail, as shown in FIGS. 8 and 9, the protruding portion 44 of the channel tube connecting member 22A is formed by providing a cutout having a squared U-shape at a thin-wall portion of the channel tube connecting member 22A, for example, and is plastic-deformed by pulling out the protruding portion 44 toward the outer circumferential surface side. Furthermore, the plastic-deformed protruding portion 44 has an elastic force while being formed integrally with the channel tube connecting member 22A.

On the other hand, the stepped portion 43 of the bending piece member 23A is formed in a groove shape and configured by including a contacting surface 43a which is a part of the inner circumferential surface in a longitudinal direction and a wall portion 43b formed along the direction perpendicular to the contacting surface 43a.

In the endoscope 2 thus configured, when the bending piece member 23A is completely fitted in the rear end portion 21A of the distal end rigid member 21 and fixed thereto similarly as in the first embodiment, the protruding portion 44 of the channel tube connecting member 22A contacts the contacting surface 43a of the bending piece member 23A due to the elastic force of the protruding portion 44 in the present embodiment, as shown in FIG. 9.

At this time, the protruding portion 44 constantly is biased, due to the elastic force itself, toward the direction of the outer circumferential surface side, which enables the contact between the protruding portion and the contacting surface 43a of the bending piece member 23A to be surely maintained. That is, it is possible to ensure the conduction state between the channel tube connecting member 22A and the bending piece member 23A.

Needless to say, even when the adhesive is peeled off due to aging degradation and the like, and the bending piece member 23A comes off from the distal end rigid member 21 at the distal end portion 11 of the endoscope 2, according to the endoscope 2 of the present embodiment, the protruding portion 44 of the channel tube connecting member 22A slides on the contacting surface 43a and abuts the wall portion 43b of the bending piece member 23A, to be latched thereto, thereby capable of preventing movement of the bending piece member 23A in the pull-out direction from the distal end rigid member 21 (which is a direction away from the distal end rigid member 21 and the rear end side direction (right direction in FIG. 9) of the distal end rigid member 21, that is, a fall-off prevention function for preventing the bending piece member 23A from coming off from the distal end portion 11 can be obtained.

Therefore, according to the second embodiment, the same effects as those in the first embodiment can be obtained.

Note that, in the first and the second embodiments, the shapes of the stepped portions 40, 43, and the shapes of the protruding portions 41, 44 are not limited to the shapes shown in FIGS. 3 and 9, and the stepped portions and the protruding portions may have any shapes as long as the conduction state between the channel tube connecting member 22 and the bending piece member 23 can be surely maintained.

For example, it is desired to obtain only a conduction function without taking a fall-off prevention function and a positioning function into consideration, a protruding portion may be configured such that both end portions thereof are fixed, a center portion protrudes toward the inner circumferential surface side or the outer circumferential surface side, and the center portion elastically deforms.

In addition, if the endoscope according to the present invention is not limited to various kinds of endoscopes configured to be inserted into a body cavity but is configured, in particular, as a transnasal endoscope which performs treatment and therapy by inserting an insertion portion through the mouse or nasally inserting the insertion portion from the nose, it would be effective for reducing the diameter size of the distal end portion.

As described above, according to the endoscopes of the above-described respective embodiments, size reduction of the diameter of the distal end rigid member and the conduction with respect to the bending piece of the bending portion can be surely achieved.

The present invention is not limited to the above-described embodiments and modified examples, but various modifications thereof are possible as long as the gist of the present invention is not changed.

What is claimed is:

1. An endoscope comprising:
   a distal end rigid member made of resin and including a communicating hole for an insertion channel;
   a channel tube connecting member formed in a tubular shape using a member having conductivity, the channel tube connecting member having a distal end side fitted and fixed in the communicating hole of the distal end rigid member and a rear end side connected to an insertion channel tube;
   a bending piece member formed in a tubular shape using a member having conductivity, the bending piece member being fixed to just behind a rear end side of the distal end rigid member with the channel tube connecting member being housed inside the bending piece member; and
   a protruding portion provided on a circumferential surface of one of the channel tube connecting member and the bending piece member and configured to elastically protrude toward a circumferential surface of the other of the channel tube connecting member and the bending piece member, the protruding portion contacting the circumferential surface of the other of the channel tube connecting member and the bending piece member to establish conduction when the bending piece member is fixed to the distal end rigid member with the channel tube connecting member being housed inside of the bending piece member;
   wherein the protruding portion is provided on an inner circumferential surface of the bending piece member, and the channel tube connecting member includes a stepped portion provided on a part of an outer circumferential surface in a longitudinal direction, and
   when the bending piece member is fixed to the distal end rigid member with the channel tube connecting member being housed inside of the bending piece member, a distal end of the protruding portion contacts the stepped portion to establish conduction.

2. The endoscope according to claim 1, wherein the protruding portion is plastic-deformed by pushing out a part of a thin-wall portion of the bending piece member toward an inner circumferential surface side and configured integrally with the bending piece member.

3. The endoscope according to claim 1, wherein a cutout formed in a longitudinal direction is provided on the rear end side of the distal end rigid member, and the protruding portion contacts the stepped portion within a range of the cutout in the longitudinal direction.

4. The endoscope according to claim 1, wherein the protruding portion latches to the stepped portion when contacting the stepped portion, to thereby prevent the bending piece member from moving in a pull-out direction from the distal end rigid member.

5. The endoscope according to claim 1, wherein another protruding portion is provided at a position different from a position of the protruding portion provided on the inner circumferential surface of the bending piece member, and a groove portion into which the protruding portion is latched is provided on an outer circumferential surface of the distal end rigid member.

6. The endoscope according to claim 1, wherein the distal end rigid member includes inside thereof an image pickup apparatus, and the protruding portion and the stepped portion are arranged at positions separated away from the image pickup apparatus on a cross section in a direction perpendicular to a direction of an axis of the distal end rigid member.

7. An endoscope comprising:
   a distal end rigid member made of resin and including a communicating hole for an insertion channel;
   a channel tube connecting member formed in a tubular shape using a member having conductivity, the channel tube connecting member having a distal end side fitted and fixed in the communicating hole of the distal end rigid member and a rear end side connected to an insertion channel tube;

a bending piece member formed in a tubular shape using a member having conductivity, the bending piece member being fixed to just behind a rear end side of the distal end rigid member with the channel tube connecting member being housed inside the bending piece member; and a protruding portion provided on a circumferential surface of one of the channel tube connecting member and the bending piece member and configured to elastically protrude toward a circumferential surface of the other of the channel tube connecting member and the bending piece member, the protruding portion contacting the circumferential surface of the other of the channel tube connecting member and the bending piece member to establish conduction when the bending piece member is fixed to the distal end rigid member with the channel tube connecting member being housed inside of the bending piece member;

wherein the protruding portion is provided on an outer circumferential surface of the channel tube connecting member and the bending piece member includes a stepped portion provided on a part of an inner circumferential surface in a longitudinal direction, and when the bending piece member is fixed to the distal end rigid member with the channel tube connecting member being housed inside of the bending piece member, a distal end of the protruding portion contacts the stepped portion to establish conduction.

8. The endoscope according to claim 7, wherein the protruding portion is plastic-deformed by pulling out a part of a thin-wall portion of the channel tube connecting member and configured integrally with the channel tube connecting member.

* * * * *